United States Patent
McCullough

(10) Patent No.: US 9,028,443 B2
(45) Date of Patent: May 12, 2015

(54) WEEPING BALLOON CATHETER WITH DRUG DELIVERY BALLOON IN FLUID COMMUNICATION WITH COMBINATION LUMEN

(71) Applicant: Cook Medical Technologies LLC, Bloomington, IN (US)

(72) Inventor: Adam Brian McCullough, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 0 days.

(21) Appl. No.: 14/257,250

(22) Filed: Apr. 21, 2014

(65) Prior Publication Data

US 2015/0005743 A1 Jan. 1, 2015

Related U.S. Application Data

(60) Provisional application No. 61/841,587, filed on Jul. 1, 2013.

(51) Int. Cl.
*A61M 31/00* (2006.01)
*A61M 25/10* (2013.01)
*A61M 25/09* (2006.01)

(52) U.S. Cl.
CPC ........... *A61M 25/1011* (2013.01); *A61M 25/09* (2013.01); *A61M 2025/1013* (2013.01); *A61M 2025/105* (2013.01); *A61M 2025/1061* (2013.01); *A61M 2025/091* (2013.01)

(58) Field of Classification Search
CPC ................. A61M 2025/1013; A61M 25/1011; A61M 25/1006; A61M 2025/1061; A61M 25/1018
USPC .......... 604/101.01, 101.02, 509, 510, 103.01, 604/103.02, 102.01, 102.02
See application file for complete search history.

(56) References Cited

U.S. PATENT DOCUMENTS

| | | | |
|---|---|---|---|
| 5,295,962 A | 3/1994 | Crocker et al. | |
| 5,421,826 A * | 6/1995 | Crocker et al. | ............... 604/509 |
| 5,549,551 A | 8/1996 | Peacock, III et al. | |
| 5,843,116 A | 12/1998 | Crocker et al. | |
| 8,034,022 B2 | 10/2011 | Boatman | |
| 8,182,446 B2 | 5/2012 | Schaeffer et al. | |
| 8,348,890 B2 | 1/2013 | Gerrans et al. | |
| 2010/0120620 A1 | 5/2010 | Chalivendra et al. | |
| 2010/0249702 A1 | 9/2010 | Magana et al. | |
| 2012/0143054 A1 | 6/2012 | Eaton et al. | |
| 2012/0310085 A1 | 12/2012 | Herweck et al. | |
| 2013/0165769 A1* | 6/2013 | Gerrans et al. | ................ 600/424 |

* cited by examiner

*Primary Examiner* — Bhisma Mehta
*Assistant Examiner* — Hamza Darb
(74) *Attorney, Agent, or Firm* — Liell & McNeil

(57) ABSTRACT

A weeping balloon catheter includes a catheter having an elongate tubular body defining an inflation lumen and a combination lumen that terminates at an open distal end of the elongate tubular body. A dilation balloon is disposed at a distal end of the elongate tubular body and is in fluid communication with the inflation lumen. A drug delivery balloon is disposed at least partially over the dilation balloon and includes at least one drug release opening through an outer wall of the drug delivery balloon. The drug delivery balloon is in fluid communication with the combination lumen through a sidewall opening of the elongate tubular body.

20 Claims, 3 Drawing Sheets

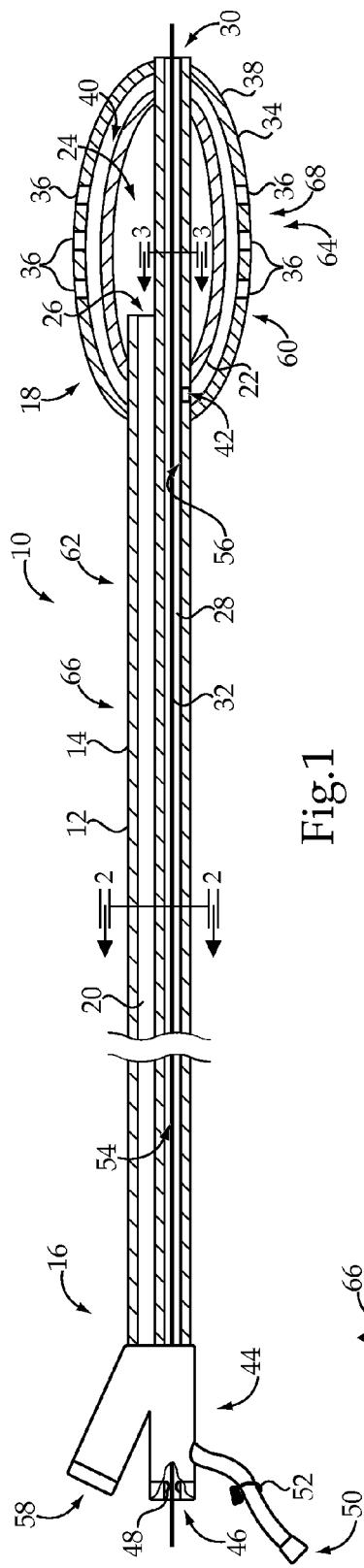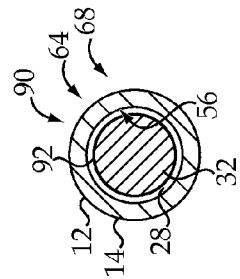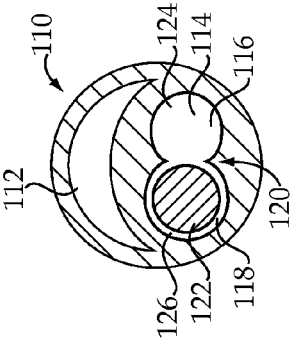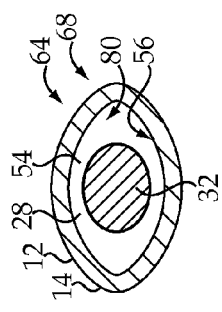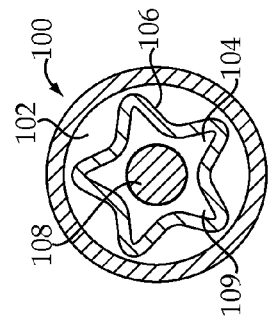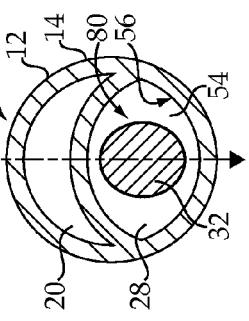

WEEPING BALLOON CATHETER WITH DRUG DELIVERY BALLOON IN FLUID COMMUNICATION WITH COMBINATION LUMEN

TECHNICAL FIELD

The present disclosure relates generally to a weeping balloon catheter and more particularly to a weeping balloon catheter having a drug delivery path defined by a combination lumen and a drug delivery balloon.

BACKGROUND

Catheters provide minimally invasive means for treating various conditions. For example, angioplasty is a common procedure used to treat cardiovascular disease. During an angioplasty procedure, a medical device, such as a balloon catheter, may be percutaneously inserted into a vessel narrowed by stenosis. The balloon may be expanded at the stenosis to ultimately restore blood flow through the vessel. In some cases, a stent may be placed at the narrowed portion of the vessel to help keep the vessel open. In either case, it may be desirable to combine the balloon and/or stent treatment with the application of therapeutic drugs. In particular, it may be desirable to deliver a therapeutic drug exclusively to the narrowed portion of the vessel. In some cases, a therapeutic drug may be used to reduce restenosis at the treatment site.

A number of catheter devices have been developed to administer a therapeutic agent locally to tissue while dilating a body vessel, such as during delivery of a therapeutic agent to a dilated portion of a coronary artery in an angioplasty procedure. For instance, U.S. Pat. No. 8,182,446 to Schaeffer et al. discloses a catheter having a dual balloon assembly. The dual balloon assembly includes an inner balloon and a porous outer balloon concentrically arrayed around the inner balloon. Radial outward expansion of the inner balloon may urge the outer balloon into contact with the wall of a vessel, where a therapeutic agent may be delivered from the catheter through apertures in the outer balloon. Such a balloon catheter device is also referred to as a weeping balloon. Weeping balloons typically require a profile size sufficient to accommodate a wire guide lumen, an inflation lumen, and a drug delivery lumen. Although weeping balloons have definite advantages, it should be appreciated that there is a continuing need for improved catheter devices.

The present disclosure is directed toward one or more of the problems or issues set forth above.

SUMMARY OF THE DISCLOSURE

In one aspect, a weeping balloon catheter includes a catheter having an elongate tubular body defining an inflation lumen and a combination lumen that terminates at an open distal end of the elongate tubular body. A dilation balloon is disposed at a distal end of the elongate tubular body and is in fluid communication with the inflation lumen. A drug delivery balloon is disposed at least partially over the dilation balloon and includes at least one drug release opening through an outer wall of the drug delivery balloon. The drug delivery balloon is in fluid communication with the combination lumen through a sidewall opening of the elongate tubular body.

In another aspect, a method of operating a weeping balloon catheter is provided. The weeping balloon catheter includes a catheter having an elongate tubular body defining an inflation lumen and a combination lumen that terminates at an open distal end of the elongate tubular body. The weeping balloon catheter also includes a dilation balloon disposed at a distal end of the elongate tubular body and in fluid communication with the inflation lumen, and a drug delivery balloon disposed at least partially over the dilation balloon and including at least one drug release opening through an outer wall of the drug delivery balloon. The drug delivery balloon is in fluid communication with the combination lumen through a sidewall opening of the elongate tubular body. The method includes steps of advancing the combination lumen over a wire guide toward a target site within a body lumen, and advancing a therapeutic agent along a drug delivery path defined by a first clearance between the wire guide and a wall of the combination lumen and the drug delivery balloon. The method also includes releasing the therapeutic agent from the drug delivery balloon at the target site.

BRIEF DESCRIPTION OF THE DRAWINGS

FIG. 1 is a partially sectioned side diagrammatic view of a weeping balloon catheter, according to one embodiment of the present disclosure;

FIG. 2 is a cross sectional view taken along lines 2-2 of FIG. 1;

FIG. 3 is a cross sectional view taken along lines 3-3 of FIG. 1;

FIG. 4 is a cross sectional view taken along lines 3-3 of FIG. 1, depicting a reduced clearance between a wire guide and a wall of the combination lumen;

FIG. 5 is an alternative cross sectional view of a dual lumen catheter portion of a weeping balloon catheter, according to the present disclosure;

FIG. 6 is another alternative cross sectional view of a dual lumen catheter portion of a weeping balloon catheter, according to the present disclosure;

DETAILED DESCRIPTION

Figure 7:
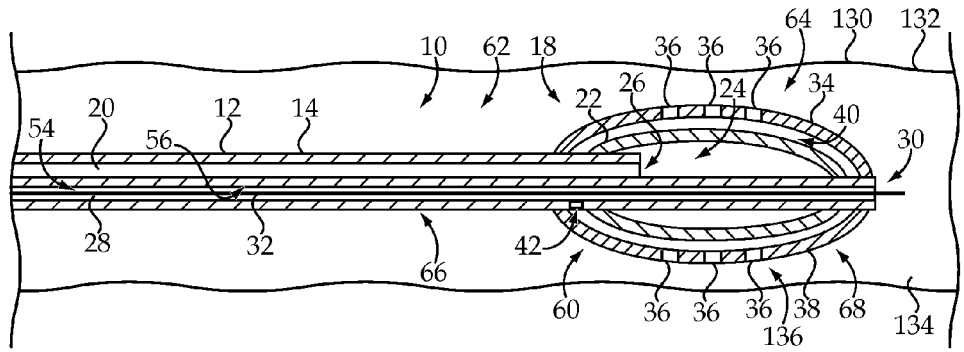
FIG. 7 is a side diagrammatic view of a vascular structure of a patient depicting one stage of a treatment procedure using the weeping balloon catheter of FIG. 1.

Referring to FIG. 1, there is shown a weeping balloon catheter 10 according to one embodiment of the present disclosure. The weeping balloon catheter 10 generally includes a catheter 12 having an elongate tubular body 14 having a proximal end 16 and a distal end 18. The elongate tubular body 14 may be made from any common medical tube material, such as, for example, polytetrafluoroethylene (PTFE), high density polyethylene (HDPE), nylon, polyetheretherketone (PEEK), or any vinyl, plastic, rubber, or silicone, and may exhibit both stiffness, or firmness, and flexibility. Materials as well as dimensions may vary depending on the particular application. In the present disclosure, "proximal" will be used to refer to the end of a component or feature that is closest to a clinician, while "distal" is used to refer to a component or feature that is farthest away from the clinician.

Such meanings are consistent with conventional use of the terms and, as such, should be understood by those skilled in the art.

The elongate tubular body 14 defines an inflation lumen 20 extending from the proximal end 16 to a dilation balloon 22 disposed, or mounted, at the distal end 18 of the elongate tubular body 14. The inflation lumen 20 may be in fluid communication with an interior space 24 of the dilation balloon 22 via one or more openings through the elongate tubular body 14. For example, the inflation lumen 20 may terminate at an open distal end, or first distal opening, 26 of the elongate tubular body 14 that is in fluid communication with the interior space 24 of the dilation balloon 22.

The elongate tubular body 14 also defines a combination lumen 28 extending from the proximal end 16 to an open distal end, or second distal opening, 30 of the elongate tubular body 14. The combination lumen 28 may have various uses. For example, the combination lumen 28 may be used for advancing the weeping balloon catheter 10 over a wire guide 32 during a treatment procedure. Further, according to the present disclosure, the combination lumen 28 may be used as an infusion pathway, as will be described below.

A drug delivery balloon 34 may be disposed at least partially over the dilation balloon 22, according to a nested arrangement, and may include at least one drug release opening 36 through an outer wall 38 of the drug delivery balloon 34. According to some embodiments, an array of drug release openings 36 may be provided. The drug delivery balloon 34 or, more particularly, an interior 40 of the drug delivery balloon 34, is in fluid communication with the combination lumen 28 through a sidewall opening 42 of the elongate tubular body 14. Although only a single sidewall opening 42 is shown, it should be appreciated that additional fluid connections between the combination lumen 28 and the interior 40 of the drug delivery balloon 34 may be provided.

A proximal fitting 44 may provide an interface for communicating with one or both of the inflation lumen 20 and the combination lumen 28, in a manner known to those skilled in the art. For example, the proximal fitting 44 may include two separate openings that are both in fluid communication with the combination lumen 28. A first sealed opening 46 may include a sealing member 48 and may be configured for receiving the wire guide 32, and a second selectively actuated opening 50 may be configured for receiving a therapeutic agent. For example, a clamp, valve, or other similar member 52 may be provided for fluidly opening or closing a fluid connection between the second selectively actuated opening 50 and the combination lumen 28.

Figure 9:
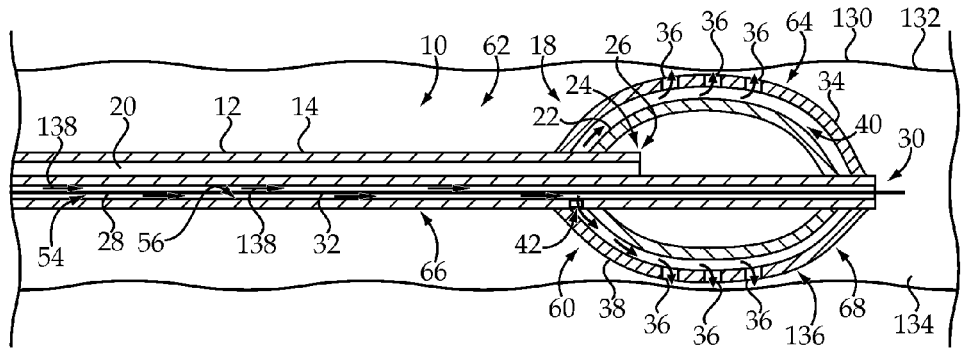
FIG. 9 is a side diagrammatic view of the vascular structure at another procedure stage.

The wire guide 32 may be received within the combination lumen 28 during advancement of the combination lumen 28 over the wire guide 32. A liquid source may be fluidly connected with the proximal fitting 44 and may provide a liquid, such as a therapeutic agent, through the second selectively actuated opening 50 and along a drug delivery path defined by a first clearance 54 between the wire guide 32 and a wall 56 of the combination lumen 28 and the drug delivery balloon 34. Leakage at the first opening 46 may be reduced using the sealing member 48. As should be appreciated, the drug delivery path, which is depicted in FIG. 9 and discussed below, also includes the sidewall opening 42 of the elongate tubular body 14.

The proximal fitting 44 may include an additional opening 58 for advancement of a fluid from a fluid source, through the inflation lumen 20, and into the dilation balloon 22. In particular, a desirable inflation medium may be advanced through the additional opening 58, through the inflation lumen 20, through the open distal end 26, and into the interior space 24 of the dilation balloon 20. The fluid may transition the dilation balloon 22 from a collapsed state to an expanded state, in a manner known to those skilled in the art.

As shown, the sidewall opening 42 may be proximal to the dilation balloon 22, for reasons that will become more apparent below. In addition, the sidewall opening 42 may be proximal to a transition 60 of the catheter 12 from a dual lumen catheter, or catheter portion, 62 to a single lumen catheter, or catheter portion, 64. The dual lumen catheter portion 62 may correspond to a proximal portion 66 of the catheter 12, while the single lumen catheter portion 64 may correspond to a distal portion 68 of the catheter 12. The single lumen catheter portion 64 may correspond in length with the portion of the catheter 12 supporting the dilation balloon 22 and, as such, the single lumen catheter portion 64 may be much shorter in length than the dual lumen catheter portion 62. According to some embodiments, no more than two lumens (i.e., the inflation lumen 20 and the combination lumen 28) may be provided. In other words, the dual lumen catheter portion 62 may include exactly two lumens including the inflation lumen 20 and the combination lumen 28.

Turning now to FIG. 2, which depicts a cross section taken along lines 2-2 of FIG. 1, the dual lumen catheter portion 62 may include the inflation lumen 20 and the combination lumen 28 arranged in a side-by-side configuration. According to this exemplary embodiment, the inflation lumen 20 may have a crescent shape, while the combination lumen 28 may have a substantially oval shape. The oval shape may provide additional clearance, shown at 80, on opposing sides of axis A. In particular, when the wire guide 32, which typically will have a cylindrical shape, is received within the combination lumen 28, the additional clearance at 80 makes up a majority of the first clearance 54. Of course, alternative shapes and configurations of the inflation lumen 20 and the combination lumen 28 are contemplated.

FIG. 3 depicts a cross section taken along lines 3-3 of FIG. 1 and represents the single lumen catheter portion 64 of the weeping balloon catheter 10. According to some embodiments, a distal segment 90 of the catheter 12, corresponding to the single lumen catheter portion 64 of the catheter 12, may have a reduced clearance 92, shown in FIG. 4, between the wire guide 32 and the wall 56 of the combination lumen 28 that is less than the first clearance 54. For example, in an expanded state of the dilation balloon 22, the dilation balloon 22 may radially, or inwardly, compress the wall 56 of the combination lumen 28 to define the reduced clearance 92. The distal segment 90, which includes the reduced clearance 92, may be positioned between the sidewall opening 42 and the open distal end 30. This reduced clearance 92 may reduce leakage through the open distal end 30.

According to alternative embodiments, and as shown in FIG. 5, a dual lumen catheter portion 100, which may be substituted for the dual lumen catheter portion 62 described above, may include an inflation lumen 102 and a combination lumen 104 arranged in a coaxial configuration. For example, a wall 106 defining the combination lumen 104 may be non-circular or star-shaped, as shown, and may be configured for receiving a wire guide 108 therethrough. According to some embodiments, a clearance 109 between the wall 106 and the wire guide 108 may be increased by radially, or outwardly, expanding the wall 106 using a therapeutic agent, or other liquid, advanced through the combination lumen 104. This increase in flow area and, as a result, flow rate of an infusion liquid through the combination lumen 104 may occur if the inflation lumen 102 is not at a relatively high pressure or is at a negative pressure.

According to yet another embodiment of the present disclosure, shown in FIG. 6, a dual lumen catheter portion 110 may include an inflation lumen 112 and a combination lumen 114 arranged in a side-by-side configuration. However, as opposed to the side-by-side configuration shown in FIG. 2, the combination lumen 114 of FIG. 6 may include abutting or overlapping circular openings 116 and 118, along with a wire guide retention feature 120 for restricting movement of a wire guide 122 relative to a high clearance infusion area 124 of the combination lumen 114. For example, a low clearance infusion area 126 may receive the wire guide 122, while the high clearance infusion area 124 defines a primary infusion path of the combination lumen 114. The wire guide retention feature 120 may restrict movement of the wire guide 122 into the higher flow of the high clearance infusion area 124.

It should be appreciated that a variety of different shapes and/or configurations exist for the inflation lumen 20 and the combination lumen 28. In particular, the combination lumen 28 may be designed to provide a desired clearance around the wire guide 32 that results in a desired flow rate of a liquid being advanced through the combination lumen 28 and into the drug delivery balloon 34. The dual lumen catheter portion 62 and the single lumen catheter portion 64 may or may not be separate extrusions. Further, the combination lumen 28 may be different or similar along the dual lumen catheter portion 62 and the single lumen catheter portion 64.

INDUSTRIAL APPLICABILITY

Turning now to FIG. 7, a percutaneous vascular procedure using the weeping balloon catheter 10 will be discussed with reference to a vascular structure 130 of a patient. Although a vascular structure 130 is shown, the present disclosure may be applicable to alternative bodily structures and lumens. The vascular structure 130, as should be appreciated, may include a vessel wall 132 defining a lumen 134. Although not shown, it should be appreciated that a clinician may first use an introducer to gain access to the vascular structure 130 in a known manner. Next, as shown in FIG. 7, the weeping balloon catheter 10 may be inserted through the introducer, over the wire guide 32, and into the vascular structure 130. In particular, the combination lumen 28 may be advanced over the wire guide 32 toward a target site 136, which may represent an area of stenosis in the vascular structure 130. The weeping balloon catheter 10 may be advanced such that the distal end 18 of the weeping balloon catheter 10 and, more particularly, the dilation balloon 22 and the drug delivery balloon 34 are positioned at the target site 136.

Figure 8:
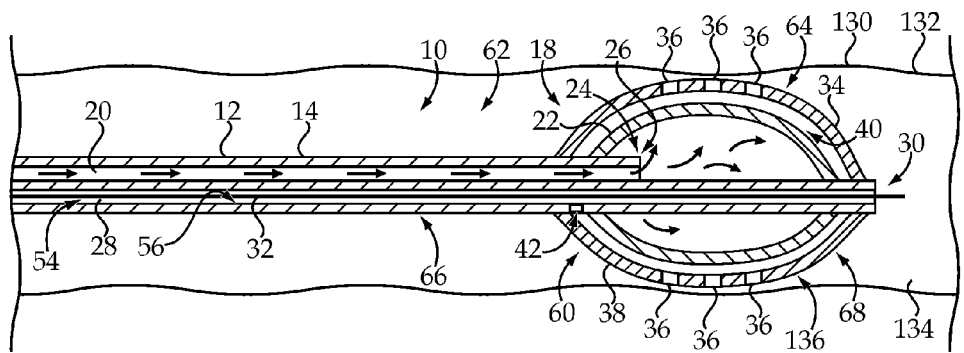
FIG. 8 is a side diagrammatic view of the vascular structure at another procedure stage.

The wire guide 32 may remain in position and, at a next stage of the procedure shown in FIG. 8, the dilation balloon 22 may be inflated to an expanded state by advancing an inflation fluid, or other media, through the inflation lumen 20. The expanded state of the dilation balloon 22 may, according to some embodiments, press outwardly against the vessel wall 132 to widen the lumen 134 at the target site 136. Further, as described above, the expanded state of the dilation balloon 22 may radially compress the wall 56 of the combination lumen 28 to define the reduced clearance 92, shown in FIG. 4.

With the dilation balloon 22 in the expanded state, a therapeutic agent, or other liquid, may be advanced along a drug delivery path 138 defined by the first clearance 54 between the wire guide 32 and the wall 56 of the combination lumen 28 and the drug delivery balloon 34, as shown in FIG. 9. In particular, the therapeutic agent may be advanced through the combination lumen 28 around the wire guide 32 and into the drug delivery balloon 34 through the sidewall opening 42.

According to some embodiments, the sidewall opening 42 may be positioned proximal to the reduced clearance 92. That is, the sidewall opening 42 may, according to some embodiments, be positioned proximal to the dilation balloon 22 and/or the transition 60 of the catheter 12 from the dual lumen catheter 62 to the single lumen catheter 64.

In some cases, leakage of the therapeutic agent through the open distal end 30 may be reduced using the reduced clearance 92 described herein. It should be appreciated that the reduced clearance 92 may be pre-formed or may be provided dynamically, such as by inflation of the dilation balloon 22, as described above. However, it should be noted that inflation of the dilation balloon 22 is not required for infusion. Further, it should be noted that the reduced clearance 92 may not be required. The sidewall opening 42 may be configured such that a majority of the therapeutic agent, or alternative liquid, flows from the first clearance 54 into the drug delivery balloon 34. Ultimately, the therapeutic agent may be released from the drug delivery balloon 34 through drug release openings 36 at the target site 136.

The shape and/or configuration of the combination lumen 28 may be varied depending on the performance characteristics desired. For example, as shown in FIG. 2, the inflation lumen 20 and the combination medical device lumen 28 may be provided in a side-by-side configuration, and the combination medial device and infusion lumen 28 may have an oval shape to provide additional clearance 80 at opposing sides of the wire guide 32. According to another side-by-side configuration, as shown in FIG. 6, the combination lumen 114 may include abutting or overlapping circular openings 116 and 118, along with a wire guide retention feature 120 for restricting movement of a wire guide 122 relative to the high clearance infusion area 124. According to a coaxial configuration of FIG. 5, the clearance 109 between the wall 106 and the wire guide 108 may be increased by radially, or outwardly, expanding the wall 106 using a therapeutic agent, or other liquid, advanced through the combination lumen 104.

Figure 10:
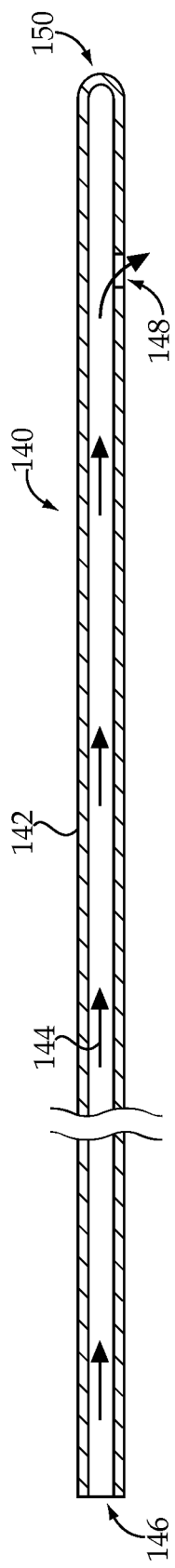
FIG. 10 is a cross sectional view of a specialty wire that may be used with the weeping balloon catheter of the present disclosure.

As an alternative to the use of the standard wire guide 32 described above, a specialty wire may be used as a substitute for, or in addition to, the standard wire guide 32. For example, as shown in FIG. 10, a first specialty wire 140 may be sized for receipt within the combination lumen 28 and may include a hollow tubular body 142. The hollow tubular body 142 may define a drug delivery path 144 extending from an open proximal end 146 to one or more side openings 148 and may have a closed distal end 150. When the specialty wire 140 is received within the combination lumen 28, the one or more side openings 148 may be substantially aligned with the one or more sidewall openings 42. As such, a liquid source may be fluidly connected to the open proximal end 146 to deliver a liquid, such as a therapeutic agent, through the hollow tubular body 142, through aligned openings 148 and 42, and into the drug delivery balloon 34. Use of the specialty wire 140 defining the drug delivery path 144 and having the closed distal end 150 may reduce leakage through the open distal end 30 of the catheter 12, particularly with minimal clearance between the specialty wire 140 and wall 56 at the openings 148 and 42.

Figure 11:
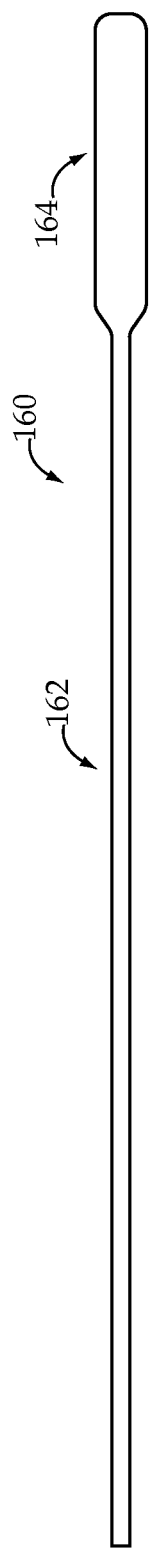
FIG. 11 is a side view of another specialty wire that may be used with the weeping balloon catheter of the present disclosure.

An alternative specialty wire that may be used with the weeping balloon catheter 10 disclosed herein is shown at 160 in FIG. 11. The specialty wire 160 may be used instead of the standard wire guide 32 and may define a drug delivery path between the specialty wire 160 and the wall 56 similar to that described above with respect to the standard wire guide 32. A proximal segment 162 of the specialty wire 160 may have a profile, or diameter, that is less than that of the standard wire guide 32 to define the first clearance 54 described above. The proximal segment 162 may transition to a distal segment 164 having an increased profile, or diameter, which may be similar to that of the standard wire guide 32. When the specialty wire 160 is received within the combination lumen 28, the transition between the proximal and distal segments 162 and 164 may be distally spaced from the side opening 42. According to some embodiments, the distal segment 164 may define the reduced clearance 92 described above. As such, leakage through the open distal end 30 of the catheter 12 may be reduced.

The weeping balloon catheter of the present disclosure permits a lower profile than conventional weeping balloon catheters. In particular, the disclosed weeping balloon catheter utilizes a common lumen for receiving a wire guide and advancing, or infusing, a therapeutic agent. In particular, according to some embodiments, the drug delivery path may be defined by a clearance between the wire guide and the wall defining the combination lumen. An additional advantage may include a simplification of the manufacturing process, since only two lumens are required at the dual lumen catheter portion of the weeping balloon catheter. Further, by infusing around the wire guide, and without requiring flushing of a conventional infusion lumen, procedure time and complexity may be reduced.

It should be understood that the above description is intended for illustrative purposes only, and is not intended to limit the scope of the present disclosure in any way. Thus, those skilled in the art will appreciate that other aspects of the disclosure can be obtained from a study of the drawings, the disclosure and the appended claims.

What is claimed is:

1. A weeping balloon catheter, comprising:
a catheter having an elongate tubular body defining an inflation lumen and a combination lumen, wherein the combination lumen terminates at an open distal end of the elongate tubular body;
a dilation balloon mounted on the elongate tubular body and in fluid communication with the inflation lumen; and
a drug delivery balloon disposed at least partially over the dilation balloon and including at least one drug release opening through an outer wall of the drug delivery balloon, wherein the drug delivery balloon is in fluid communication with the combination lumen through a sidewall opening of the elongate tubular body.

2. The weeping balloon catheter of claim 1, further including a wire guide received within the combination lumen, wherein a drug delivery path of the weeping balloon catheter is defined by a first clearance between the wire guide and a wall of the combination lumen and the drug delivery balloon.

3. The weeping balloon catheter of claim 2, wherein the sidewall opening is proximal to the dilation balloon.

4. The weeping balloon catheter of claim 2, wherein the sidewall opening is proximal to a transition of the catheter from a dual lumen catheter to a single lumen catheter.

5. The weeping balloon catheter of claim 2, wherein a distal segment of the catheter has a reduced clearance between the wire guide and the wall of the combination lumen that is less than the first clearance, wherein the distal segment is positioned between the sidewall opening and the open distal end.

6. The weeping balloon catheter of claim 5, wherein, in an expanded state of the dilation balloon, the dilation balloon radially compresses the wall of the combination lumen to define the reduced clearance.

7. The weeping balloon catheter of claim 2, wherein the catheter includes a transition from a dual lumen catheter corresponding to a proximal portion of the catheter to a single lumen catheter corresponding to a distal portion of the catheter.

8. The weeping balloon catheter of claim 7, wherein the dual lumen catheter includes the inflation lumen and the combination lumen arranged in a side-by-side configuration.

9. The weeping balloon catheter of claim 8, wherein the combination lumen includes a wire guide retention feature for restricting movement of the wire guide relative to a high clearance infusion area of the combination lumen.

10. The weeping balloon catheter of claim 7, wherein the dual lumen catheter includes the inflation lumen and the combination lumen arranged in a coaxial configuration.

11. The weeping balloon catheter of claim 2, wherein a distal segment of the wire guide has an increased profile relative to a proximal segment of the wire guide.

12. The weeping balloon catheter of claim 1, further including a wire guide received within the combination lumen, wherein a drug delivery path of the weeping balloon catheter is defined by a hollow tubular body of the wire guide and the drug delivery balloon.

13. A method of operating a weeping balloon catheter, the weeping balloon catheter including a catheter having an elongate tubular body defining an inflation lumen and a combination lumen, wherein the combination lumen terminates at an open distal end of the elongate tubular body, a dilation balloon mounted on the elongate tubular body and in fluid communication with the inflation lumen, and a drug delivery balloon disposed at least partially over the dilation balloon and including at least one drug release opening through an outer wall of the drug delivery balloon, wherein the drug delivery balloon is in fluid communication with the combination lumen through a sidewall opening of the elongate tubular body, the method comprising steps of:
advancing the combination lumen over a wire guide toward a target site within a body lumen;
advancing a therapeutic agent along a drug delivery path defined by a first clearance between the wire guide and a wall of the combination lumen and the drug delivery balloon; and
releasing the therapeutic agent from the drug delivery balloon at the target site.

14. The method of claim 13, wherein the step of advancing the therapeutic agent includes advancing the therapeutic agent through the sidewall opening positioned proximal to the dilation balloon.

15. The method of claim 13, wherein the step of advancing the therapeutic agent includes advancing the therapeutic agent through the sidewall opening positioned proximal to a transition of the catheter from a dual lumen catheter to a single lumen catheter.

16. The method of claim 13, further including reducing leakage of the therapeutic agent through the open distal end using a reduced clearance between the wire guide and the wall of the combination lumen that is less than the first clearance.

17. The method of claim 16, further including inflating the dilation balloon to an expanded state, and radially compressing the wall of the combination lumen using the dilation balloon to define the reduced clearance.

18. The method of claim 13, wherein the step of advancing the therapeutic agent includes increasing the first clearance by radially expanding the wall of the combination lumen using the therapeutic agent.

19. The method of claim 18, further including advancing the therapeutic agent through the combination lumen arranged coaxially with the inflation lumen.

20. The method of claim 13, further including restricting movement of the wire guide relative to a high clearance infusion area of the combination lumen using a wire guide retention feature of the combination lumen.

* * * * *